(12) United States Patent
Elhabashy

(10) Patent No.: US 7,621,009 B2
(45) Date of Patent: Nov. 24, 2009

(54) SURGICAL COORDINATOR FOR ANESTHESIOLOGIST AND METHODS OF USE

(76) Inventor: Basim Elhabashy, 10386 E. Sierra, Clovis, CA (US) 93619

( * ) Notice: Subject to any disclaimer, the term of this patent is extended or adjusted under 35 U.S.C. 154(b) by 279 days.

(21) Appl. No.: 11/281,717

(22) Filed: Nov. 16, 2005

(65) Prior Publication Data

US 2007/0107130 A1 May 17, 2007

(51) Int. Cl.
*A61G 13/12* (2006.01)
*A61B 19/00* (2006.01)
*A61M 25/02* (2006.01)
*F16L 3/08* (2006.01)

(52) U.S. Cl. .............................. 5/622; 5/621; 5/503.1; 5/658; 248/68.1; 248/74.3; 604/179

(58) Field of Classification Search ............... 5/622, 5/621, 632, 636, 639, 640, 652, 657, 485, 5/495, 496, 500, 502, 503.1, 658; 128/849–854, 128/872; 248/68.1, 74.1–74.5; 604/179, 604/180

See application file for complete search history.

(56) References Cited

U.S. PATENT DOCUMENTS

| | | | | |
|---|---|---|---|---|
| 3,630,195 A | * | 12/1971 | Santomieri | 604/180 |
| 3,721,234 A | * | 3/1973 | Hadtke et al. | 128/852 |
| 3,834,380 A | * | 9/1974 | Boyd | 604/180 |
| 4,040,418 A | * | 8/1977 | Collins | 128/852 |
| 4,308,642 A | * | 1/1982 | Heyman | 24/306 |
| 4,323,062 A | * | 4/1982 | Canty | 128/852 |
| 4,334,529 A | * | 6/1982 | Wirth | 128/852 |
| 4,445,894 A | * | 5/1984 | Kovacs | 604/179 |
| 4,476,860 A | * | 10/1984 | Collins et al. | 128/853 |
| 4,484,914 A | * | 11/1984 | Brown | 604/180 |
| 4,553,538 A | * | 11/1985 | Rafelson | 128/852 |
| 4,570,628 A | * | 2/1986 | Neal | 128/853 |
| 4,591,356 A | * | 5/1986 | Christie | 604/179 |
| 4,596,245 A | * | 6/1986 | Morris | 128/852 |
| 4,605,397 A | * | 8/1986 | Ligon et al. | 604/179 |
| 4,664,103 A | * | 5/1987 | Martin et al. | 128/852 |
| 4,665,566 A | * | 5/1987 | Garrow | 2/171 |
| 4,702,736 A | * | 10/1987 | Kalt et al. | 604/180 |
| 4,720,881 A | | 1/1988 | Meyers | |
| 4,738,662 A | * | 4/1988 | Kalt et al. | 604/180 |
| 4,795,429 A | * | 1/1989 | Feldstein | 604/80 |

(Continued)

*Primary Examiner*—Robert G Santos
(74) *Attorney, Agent, or Firm*—Robert M. Downey, PA

(57) ABSTRACT

The present invention is an organizational kit designed to help anesthesiologists when providing anesthesia during major surgery such as heart, thoracic, major vascular, and/or major abdominal. The invention helps the anesthesiologist organize the different intravenous and arterial lines, catheters, monitoring cables, pressure transducers and other devices coming from or going to the patient. It also serves as an educational tool for new anesthesia students, residents, fellows and new graduate anesthesiologists to help them understand how to connect the different ports coming out from the distal end of a Swan-Ganz catheter to their matching cables, monitor lines and transducers. The invention may serve as a reference for the doses and methods of administering common drugs used by the anesthesiologist intraoperatively. The invention also helps the practitioner set up the different modes of a pacemaker machine. The invention is designed to travel with the patient from the operating room to the recovery room and intensive care units, carrying all the lines, catheters, monitoring cables and devices, and holding them in place to prevent accidental dislodgement. Pockets are provided to hold a pacemaker, emergency medications, laryngoscope and endotracheal tube, and/or other devices that may be needed in an emergency situation during transport.

11 Claims, 9 Drawing Sheets

U.S. PATENT DOCUMENTS

| | | | | |
|---|---|---|---|---|
| 4,838,878 | A * | 6/1989 | Kalt et al. | 604/180 |
| 4,944,311 | A * | 7/1990 | Eldridge et al. | 128/849 |
| 4,988,062 | A | 1/1991 | London | |
| 4,988,338 | A * | 1/1991 | Taylor et al. | 604/180 |
| 5,010,899 | A * | 4/1991 | Thompson | 128/849 |
| 5,036,866 | A * | 8/1991 | Eldrige et al. | 128/849 |
| 5,037,397 | A * | 8/1991 | Kalt et al. | 604/174 |
| 5,074,316 | A * | 12/1991 | Dowdy | 128/849 |
| 5,082,111 | A * | 1/1992 | Corbitt et al. | 206/363 |
| 5,095,918 | A * | 3/1992 | Busch | 128/849 |
| 5,210,913 | A * | 5/1993 | Clark | 24/518 |
| 5,224,674 | A * | 7/1993 | Simons | 248/68.1 |
| 5,263,941 | A * | 11/1993 | Cockrill | 604/179 |
| 5,304,146 | A * | 4/1994 | Johnson et al. | 604/180 |
| 5,308,339 | A * | 5/1994 | Kalt et al. | 604/180 |
| 5,334,186 | A | 8/1994 | Alexander | |
| 5,335,677 | A * | 8/1994 | Busch | 128/852 |
| 5,339,831 | A * | 8/1994 | Thompson | 128/852 |
| 5,342,317 | A * | 8/1994 | Claywell | 604/179 |
| 5,383,476 | A * | 1/1995 | Peimer et al. | 128/849 |
| 5,435,448 | A | 7/1995 | Kempen | |
| 5,445,165 | A * | 8/1995 | Fenwick | 128/849 |
| 5,464,025 | A * | 11/1995 | Charles et al. | 128/849 |
| 5,494,051 | A | 2/1996 | Schneider, Sr. | |
| 5,496,282 | A * | 3/1996 | Militzer et al. | 604/179 |
| 5,513,655 | A * | 5/1996 | Peimer et al. | 128/849 |
| 5,624,403 | A | 4/1997 | Jaquith | |
| 5,672,159 | A * | 9/1997 | Warrick | 604/179 |
| 5,816,253 | A * | 10/1998 | Sosebee | 128/849 |
| 5,836,453 | A * | 11/1998 | Herrera | 206/702 |
| 5,897,519 | A * | 4/1999 | Shesol et al. | 602/79 |
| 5,988,172 | A * | 11/1999 | Sosebee | 128/849 |
| 6,055,987 | A * | 5/2000 | Griesbach et al. | 128/849 |
| 6,216,700 | B1 * | 4/2001 | Griesbach et al. | 128/849 |
| 6,314,959 | B1 * | 11/2001 | Griesbach et al. | 128/849 |
| 6,615,836 | B1 * | 9/2003 | Griesbach et al. | 128/849 |
| RE38,485 | E * | 4/2004 | Busch | 128/852 |
| 6,721,977 | B2 | 4/2004 | Solesbee et al. | |
| 6,874,505 | B1 * | 4/2005 | Fenwick et al. | 128/849 |
| 7,096,870 | B2 * | 8/2006 | Lamprich et al. | 128/849 |
| 7,232,427 | B2 * | 6/2007 | Propp | 604/180 |
| 7,284,729 | B2 * | 10/2007 | Walsh et al. | 248/74.3 |
| 7,284,730 | B2 * | 10/2007 | Walsh et al. | 248/74.3 |
| 7,457,506 | B1 * | 11/2008 | Osborne, II | 385/136 |
| 2003/0033675 | A1 | 2/2003 | Solesbee et al. | |
| 2003/0132352 | A1 | 7/2003 | Weaver | |
| 2004/0118410 | A1* | 6/2004 | Griesbach et al. | 128/852 |
| 2005/0061330 | A1* | 3/2005 | Fenwick et al. | 128/849 |
| 2005/0279366 | A1* | 12/2005 | Adragna | 128/849 |
| 2006/0065275 | A1* | 3/2006 | Lamprich et al. | 128/849 |
| 2006/0169290 | A1* | 8/2006 | Harris et al. | 128/852 |
| 2006/0191540 | A1* | 8/2006 | Lamprich et al. | 128/849 |
| 2007/0107130 | A1* | 5/2007 | Elhabashy | 5/622 |
| 2007/0235038 | A1* | 10/2007 | Alinsod et al. | 128/849 |
| 2008/0097334 | A1* | 4/2008 | Dikeman et al. | 604/180 |
| 2008/0163425 | A1* | 7/2008 | White | 5/603 |
| 2008/0195050 | A1* | 8/2008 | Dickert et al. | 604/180 |
| 2008/0200880 | A1* | 8/2008 | Kyvik et al. | 604/180 |

* cited by examiner

SURGICAL COORDINATOR FOR ANESTHESIOLOGIST AND METHODS OF USE

BACKGROUND OF THE INVENTION

1. Field of the Invention

The present invention relates to the providing of anesthesia during surgery, and particularly to devices and methods for coordinating and organizing the numerous patient tubes, catheters, wires, monitoring lines and other objects used by an anesthesiologist during surgery, particularly major surgery. The invention is designed to travel with the patient for use by other health care practitioners following surgery, particularly in the intensive care unit and in the recovery room.

2. Description of the Prior Art

When a patient arrives at the operating room (OR) for major surgery (such as, for example, heart, major chest, abdominal, renal or liver surgery), the anesthesiologist will ordinarily attach a host of invasive tubes, lines, catheters, wires and other devices to the patient that are used throughout the surgery and often afterwards. These include such things as one or two intravenous peripheral lines that are attached to an upper extremity of the patient; an arterial line that is attached to an arm or the groin of the patient; one or two central lines that are attached to the neck or upper chest of the patient; a cordis line that is attached to the neck or upper chest of the patient; and a Swan-Ganz catheter attached to the neck or upper chest of the patient.

During and after surgery, the patient will need drugs (such as, for example, vasopressor and other supportive drugs) some of which are administered via dripping methods, and others via injection into tubes. The patient may also require blood, plasma and other fluids. These materials and drugs may be supplied directly to the patient through the central line, or through one of the lines extending through the Swan-Ganz catheter. Depending upon which Swan-Ganz catheter is used, it may have several ports which will be connected to different tubing, monitoring cables and pressure transducers. One of these ports may also be connected to a drip line that holds several stopcocks which could receive different medications from the dripping machines to be given to the patient.

All of these lines, tubes, and catheters come from different parts of the patient body and lead around the head of the patient where the anesthesiologist is stationed during surgery. Here, the multitude of lines and tubes are connected to monitors, screens, drip lines, injection ports and other devices that the anesthesiologist must keep control of during the hours of surgery. It is easy to confuse these numerous lines and tubes. This can be dangerous in the event that an emergency situation arises during surgery where the anesthesiologist is required to quickly provide a drug or other medication to the patient. Delay by the anesthesiologist while trying to locate the correct tube to administer the drug, or inadvertent administration of a drug to the wrong site could endanger the life of the patient and affect the outcome of the surgery.

During lengthy surgery, a first anesthesiologist may be relieved by a second anesthesiologist who must step in and figure out how the tubes, lines and wires have been set up by the first anesthesiologist. Since there is no established or standard way to set up these tubes, lines and wires, the second anesthesiologist must figure out how the first anesthesiologist set everything up. If the transition from one health care practitioner to another is not smooth, there is another dangerous potential for delay or error by the second anesthesiologist in administering a needed drug during an emergency situation.

Similarly, the maze of unorganized tubes, lines, tape, labels and devices make it difficult to teach student doctors (residents and fellows).

It is also very easy for the tubes and lines to become tangled, and unless they are well secured and supported, it is possible that they can be pulled out, or become dislodged or disconnected—sometimes without the knowledge of the anesthesiologist—placing the patient in a threatening and risky situation. This is especially true for the Swan-Ganz catheter which can cause serious or potentially fatal results if dislodged.

Once surgery is completed, the patient must be transported from the operating room to an intensive care unit or elsewhere. Many of the monitors, drip lines and other tubes must remain inserted into the patient for hours or days after surgery. The simple act of transporting the patient down the hall from an operating room to an intensive care unit requires bringing all of these wires, tubes and lines along too—as well as the machines, drip bags/bottles, pacemaker, and other devices that they are connected to. There is a serious risk of pulling out a tube, line or catheter as all of these things are manipulated during transport.

Some of the devices must be disconnected while the patient is traveling, and reconnected when the patient arrives at the intensive care unit. Once the patient arrives at the intensive care unit for recovery, the nurses and other health care providers must again untangle and sort out all of the tubes and lines, and reconnect the lines and wires to their associated monitors and other devices. Some of the monitors provide critical data regarding the condition of the patient, such that any unnecessary delay in reconnecting could pose serious risks to the patient.

There are some organizational tools in the prior art that begin to address these situations, including the invention disclosed in U.S. Pat. No. 4,988,062. This patent discloses a multi-part pad with pivotally attached wings, the wings having manifold devices attached at their distal ends for receiving and separating the tubes and lines coming out of the patient. However, this device is not designed to travel with the patient, and once the tubes are placed in the manifolds, the wings may still be pivoted which could cause the tubes to be pulled out or disconnected, having potentially disastrous results. Another device disclosed in U.S. Pat. No. 5,624,403 is a removable pad that is designed to be placed across the torso of a patient, the upwardly facing surface of the pad being composed of loop pile material (such as Velcro®) for receiving corresponding strips that hold down the tubes and lines leading from the patient. However, this device is designed to stretch across the torso of the patient, and therefore cannot be used during abdominal surgery, nor can it be used by an anesthesiologist who is stationed above the head of the patient. There are also elaborate trays such as those disclosed in U.S. Pat. Nos. 4,720,881, 5,334,186 and 5,435,448. None of these prior art inventions provides an organizational guide for the numerous tubes, lines, catheters and wires used by an anesthesiologist during major surgery; none of them are designed to travel with the patient from the operating room to intensive care or elsewhere for use by other health care providers; and none of them serves as an educational tool or reference for the new anesthesia student, resident, fellow or new graduate anesthesiologist to learn about Swan-Ganz catheter usage, pacemaker modes, doses, and administration of commonly used drugs during surgery.

It is therefore desirable to provide devices and methods for coordinating and organizing the numerous patient tubes, catheters, wires, monitoring lines as well as other objects and machines (e.g., pacemaker, pressure monitors) used by an anesthesiologist during major surgery; to provide standardization for the positions of these various tubes, wires and lines so that the anesthesiologist, his/her replacement and other health care providers (particularly residents and fellows) can know instantly where everything is; to provide coordination and organization devices that prevent inadvertent disengagement of tubes, lines and wires leading from the patient during and after surgery; and to provide coordination and organization devices that can travel with the patient and remain with the patient during recovery for hours or days after surgery.

SUMMARY OF THE INVENTION

The present invention is a pad that is used in a medical operating room to coordinate and organize the many tubes, lines and catheters that are used by an anesthesiologist during surgery, especially major surgery, such as heart surgery. The pad is placed under the head of the patient, and includes a plurality of clips, straps, clamps, latches or bolts ("holders") that are used to separate and hold in place the various tubes, wires, lines, catheters and the like ("lines") leading to/from the patient. The holders are designed to keep each such line in place on the pad, while not constricting or otherwise interrupting the flow through the line.

In one aspect of the invention, the pad is made of a flexible rubberized material that does not lose strength if it becomes moist, and which may be easily wiped clean. Alternatively, the pad may be made of durable plastic or disposable paper similar to that used in hospitals for other pads.

In one aspect of the invention, the pad also includes one or more permanent labels accompanying the holders to provide standard locations for certain tubes or lines leading from/to the patient (and a diagram to show the location for the patient's head on the pad). Among other things, the diagram may show the different ports of the Swan-Ganz catheter and illustrate which port is to be connected to which line. The diagram may also show the doses and methods of administration of drugs commonly used during providing anesthesia, and may serve as a reference for the physician or health care practitioner, particularly if a drug is to be administered by infusion.

In a variation of this aspect of the invention, one or more labels may be provided for attachment to the lines held in place by the pad at locations on those lines near their sources (i.e., a duplicate label for attachment to a tube near the drip bag that the tube is attached to). Such labels may be blank or pre-printed.

In another aspect of the invention, the holders may be color coded to provide easy identification and coordination of the associated lines.

In another aspect of the invention, the pad includes one or more pockets or flaps for holding such things as a pacemaker unit, pressure monitors, emergency medication and the like.

In a variation of this embodiment, labels may be provided for these pockets.

In another aspect of the invention, one or more foldable flaps are provided along the edges of the pad for holding bundles of tubes or lines.

In another aspect of the invention, the pad may be provided in the form of a sham having a pocket or flap for receiving the pillow placed under the patient's head so that the patient rests on the pad with the pillow underneath inside.

In another aspect of the invention, an accessory case for the pacemaker machine is provided. During cardiac surgery, pacing wires are connected to the heart and then to a cable that is handed to the anesthesiologist for connection to a pacemaker machine. This machine usually hangs on a pole next to the anesthesiologist, behind the patient. The anesthesiologist usually sets up this machine to a specific mode according to the condition of the patient. These modes are complicated and easy to forget. The accessory case holds the pacemaker machine and hangs from the pole, and includes a set of instructions on the front. These instructions explain the different modes of the pacemaker, and what kind of mode the anesthesiologist should choose for the particular patient condition.

It is to be appreciated that different groupings and combinations of these various aspects and embodiments may be provided, depending on the functionality desired by the user.

The clips are organized according to the expected locations of the tubes or lines coming from the patient. These lines may originate on either the left or right side of the patient, depending on where they are inserted into the patient. In some cases, there may be two of a given line set up during surgery (e.g. the peripheral line, or the central line). Thus, a preferred embodiment of the pad provides holders with duplicate labels for these lines on both sides of the patient's head.

Other lines, particularly the arterial line and the Swan-Ganz catheter, are generally brought to the left side of the patient's head, regardless of which side of the patient the other end is connected to, so the pad of the present invention will ordinarily provide only one holder for such lines and catheters (although duplicate holders may also be provided).

The following is an exemplary, but by no means exhaustive, list of possible holders and labels provided on the pad: (a) peripheral line holders on both sides of the patient's head (leading to/from the patient's arms); (b) cordis line holders on both sides of the patient's head (leading to/from a neck vein); (c) central line holders on both sides of the patient's head (leading to/from a neck vein); (d) an arterial line holder on one side of the patient's head (leading from/to a main artery); and (e) a Swan-Ganz catheter holder on one side of the patient's head (leading to/from the heart).

The Swan-Ganz catheter may have several ports, as needed for the particular surgery involved. When a Swan-Ganz catheter having a full set of ports is used, it is generally accepted that they be connected as follows (although this convention could change with advances in the Swan-Ganz catheter or other technology): three of the ports are pressure monitor lines/ports that are ordinarily connected to pressure monitor cables (2 to cardiac cables, and one to a PA-SVO2 cable); the yellow line/pot ordinarily connects to the pulmonary artery (PA) pressure monitor cable; the blue line/port ordinarily connects to the central venous pressure (CVP) line; and the white line/port is ordinarily connected to one or more drip bags or other ports for providing particular drugs at particular dosages during and after surgery. The white line is frequently connected to an 8-port manifold, but additional ports/manifolds may also be added in series. If a Swan-Ganz catheter for minor surgery is used, it may have only a subset of ports needed for that particular surgery. However, regardless of the number of lines/ports provided on the Swan-Ganz catheter, the convention is to always connect the same color line to the same place.

A basic embodiment of the invention includes simply the pad with multiple clips attached to it. The clips may be detachable or fixedly attached to the pad. The clips may be spring loaded, specially formed or biased to clamp and hold a line or tube, or they may be provided in the form of small straps having one end that is permanently attached to the pad, and the other end being detachable using Velcro®, a snap, a button, a buckle, or the like. These small clips/straps hold the various tubes in place against the pad.

In a preferred embodiment, the pad may be pre-labeled in the vicinity of each holder to identify which line is to be placed there, or the holders themselves may be pre-labeled (to indicate what line goes there). This provides standardization, so that the holders in the same location(s) are used to hold the same lines, surgery after surgery. Additional information may be pre-printed on the pad for the manifold, including the identification and dosages of particular drugs and medications used during and after surgery. Alternatively, the pad or the holders may be provided with adjacent writing spaces where the anesthesiologist or other health care provider may hand write or attach custom labels for the lines, according to his/her desires at the time of surgery or afterwards (using stickers, a Sharpee® pen or the like).

Other embodiments of the invention provide a representation of where the head of the patient belongs, a diagram (map) showing where the various lines should be placed. The pad is sized to fit at the end of the operating table, and either or both of the side edges as well as the bottom edge of the pad may be folded/rolled up and set to surround a bundle of tubes to keep them organized. These bundles of tubes may be held in place using holders provided along the edges (with or without using the rolled portion of the pad).

Additional straps and pockets are provided in other embodiments of the pad to hold the pacemaker, emergency medication, syringes and other devices such as a laryngoscope and endotracheal tube, for situations that may develop during transport. The pacemaker and transducer are normally suspended on poles during surgery, but are transported with the patient to ICU after surgery—which is when these devices are placed in the pockets or otherwise attached to the pad of the present invention. The additional pockets allow for other tools to travel with the patient, so that the anesthesiologist may treat the patient during transport should there be any changes in patient hemodynamics or blood pressure, or in the event that any problems develop with the patient's breathing tube, etc.

A set of holders for a 3-way transducer are provided in one embodiment of the pad. This transducer is suspended form a pole during surgery, and may be disconnected from its monitor(s), taken down and strapped to the pad during transport of the patient after surgery. This will keep the PA, CVP and central lines in place, requiring fewer personnel to travel with the patient, less chance of entanglement or dislodgement of these lines from the patient, and rapid re-attachment of cables and lines to monitors upon arrival at the ICU or the recovery room.

One embodiment includes a carrying case for the pacemaker that may include operating instructions for the pacemaker provided on the outside of the case. The pacemaker is placed in the case and hung on a pole during surgery, with wires leading to the patient. When surgery is completed, the pacemaker and case are taken down from the pole and placed in the pocket on the pad for transport with the patient. Prior to transport, the transducer is detached from its monitor(s) and attached to the pad. Other devices are also temporarily disconnected from their associated overhead monitors, and will be reconnected to similar monitors when the patient arrives at the recovery room or ICU. However, many other lines will remain connected to the patient and to their associated drip bags or devices during transport. These lines may be grouped and bundled together and wrapped into one or more flaps provided on the edges of the pad to prevent entanglement or dislodgement, the flaps being closed with Velcro®, zippers, snaps, buttons or the like. Emergency medication and tools (such as a laryngoscope and endotracheal tube) may also be placed into pockets on the pad, in case they are needed during transport. Upon arrival, the disconnected lines and cables may be easily and quickly identified and attached to their respective monitors and sources. The pad may remain with the patient for hours, days or weeks, as necessary, to maintain the organization of these lines and tubes.

It is therefore an object of the present invention to provide an organizational device and methods for coordinating the numerous patient tubes, lines and other objects used by an anesthesiologist during surgery, and by other health care providers after surgery, so that the anesthesiologist or health care provider can know instantly which tube is which, in case an emergency situation arises requiring an immediate response, such as providing or changing a dosage of a drug to be sent down one of the tubes to the patient.

It is also an object of the present invention to provide an organizational device and methods for coordinating and holding in place the numerous patient tubes, lines and other objects used by an anesthesiologist during surgery, and by other health care providers after surgery, to prevent accidental dislodgement/disengagement of the tubes or lines from the patient by avoiding excessive stress on them to prevent potentially catastrophic results.

It is also an object of the present invention to provide an organizational device and methods for coordinating the numerous patient tubes, lines and other objects used by an anesthesiologist during surgery, and by other health care providers after surgery, that allows the anesthesiologist or health care provider to be relieved by another who can instantly determine where everything is.

It is a related object of the present invention to provide a standard for organizing and coordinating the numerous patient tubes, lines and other objects used by an anesthesiologist during surgery, and by other health care providers after surgery, for use in practice as well as teaching student practitioners.

It is also an object of the present invention to provide an organizational device for coordinating the numerous patient tubes, lines and other objects used by an anesthesiologist during surgery that travels with the patient after surgery from an operating room to an intensive care unit or the like, so as to reduce the chances of disruption/dislodgement of tubes and lines from the patient during transport.

It is a related object of the present invention to provide an organizational device for coordinating the numerous patient tubes, lines and other objects used by health care practitioners after surgery, particularly during patient transport and recovery following surgery.

It is a related object of the present invention to provide a standard for organizing and coordinating the numerous patient tubes, lines and other objects used by health care practitioners after surgery for use in practice as well as teaching student practitioners.

Additional objects of the invention will be apparent from the detailed descriptions and the claims herein.

DETAILED DESCRIPTION

Figure 1:
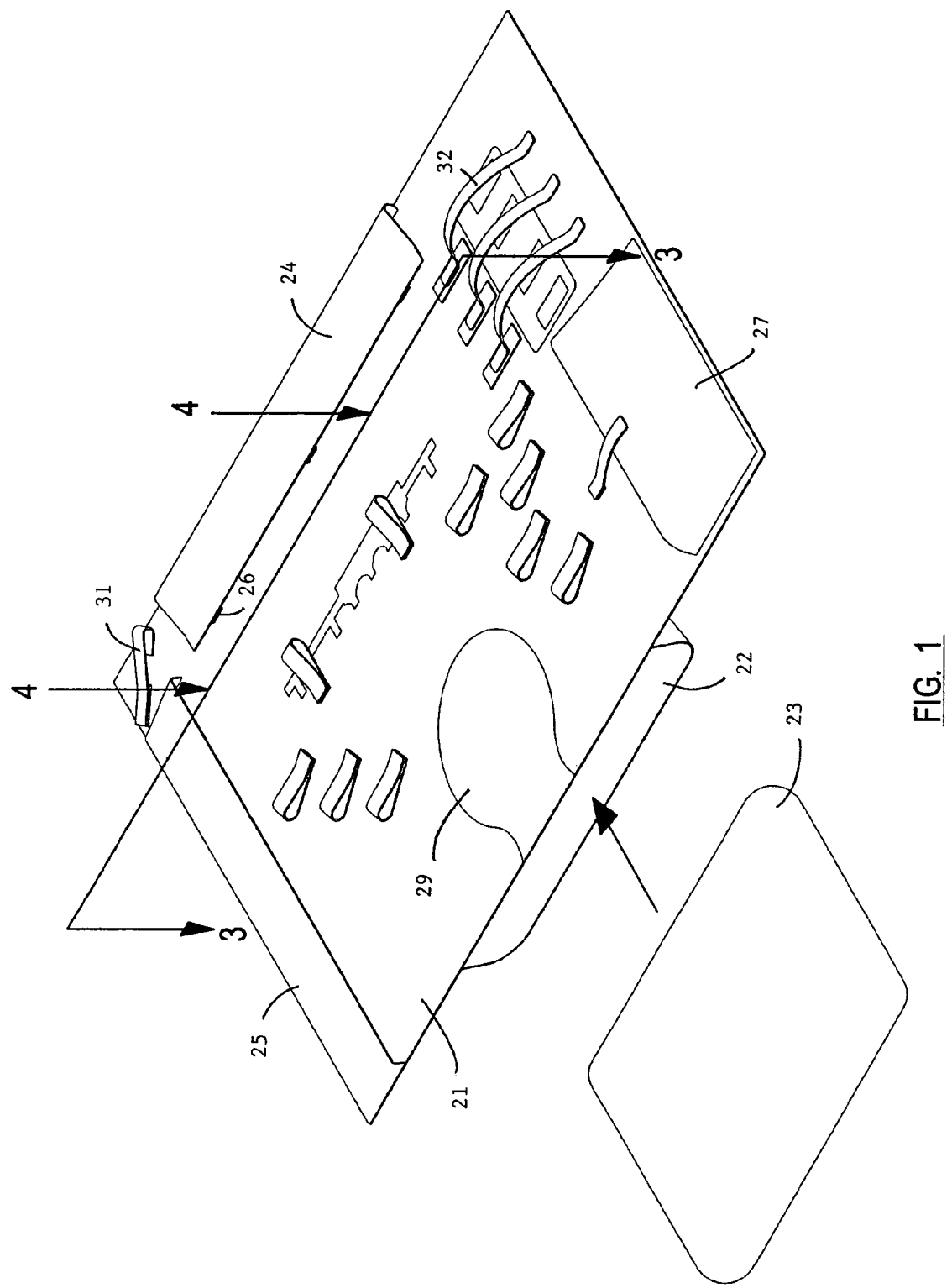
FIG. 1 is a top perspective view of an embodiment of the present invention.

Referring to the exemplary embodiment illustrated in the drawings wherein like reference characters designate like or corresponding parts throughout the several views, and referring particularly to FIG. 1, it is seen that the present invention includes a flexible pad 21 made of rubberized, plastic or paper material. The upper surface of pad 21 is provided with one or more holders 31 for holding the lines leading to/from a patient during and after surgery. The holders 31 may be detachable or fixedly attached to the pad 21. The holders 31 may be spring loaded, specially formed or biased in order to clamp and hold a line or tube, or they may be provided in the form of small straps having one end that is permanently attached to the pad, and the other end being detachable using Velcro®, a snap, a button, a buckle, or the like. These holders are used to hold the various lines and tubes in place against the pad 21, as described herein, without interrupting the flow therethrough. A diagram 29 showing the location for the patient's head may also be provided.

Figure 6:
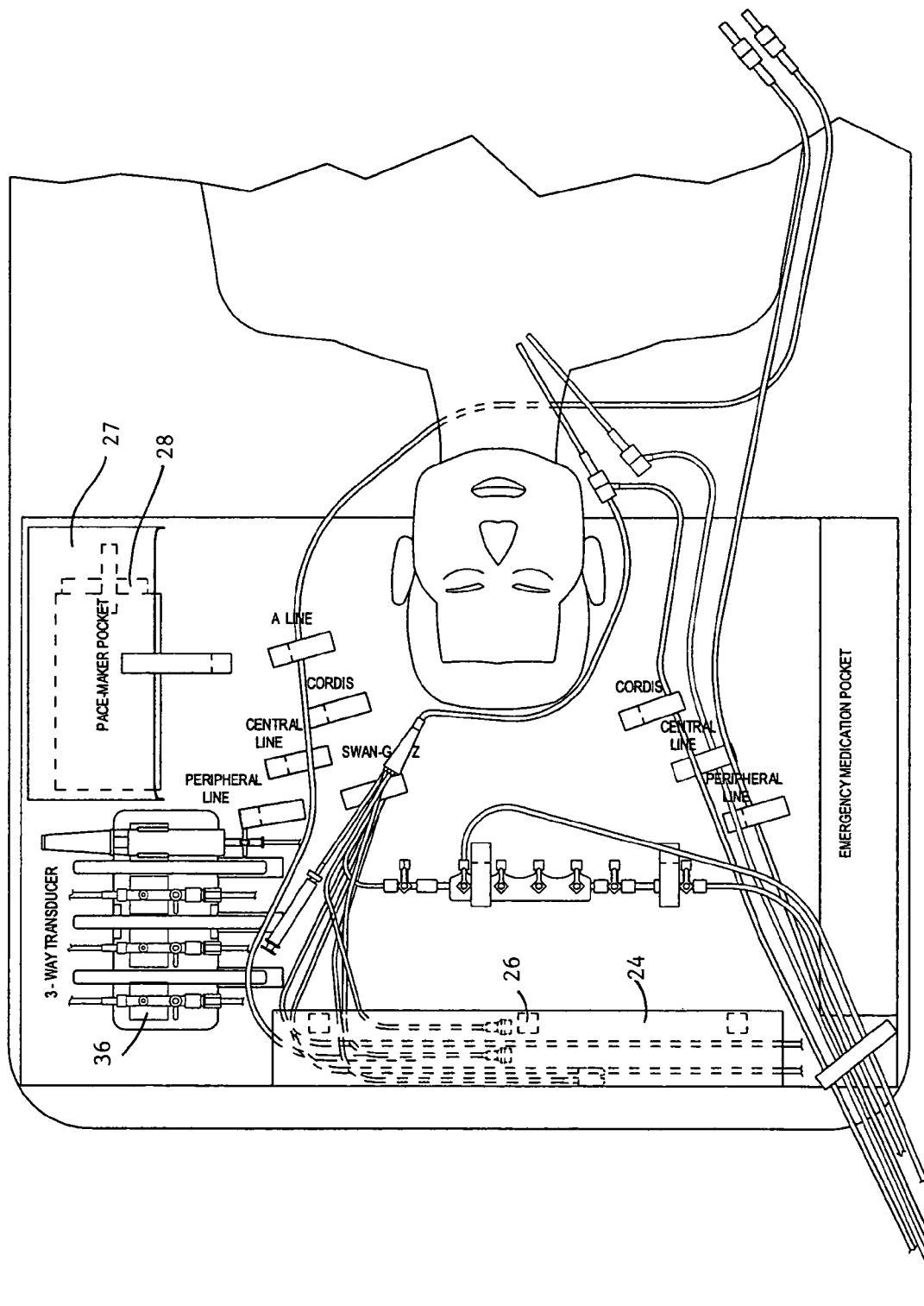
FIG. 6 is a top perspective view of an embodiment of the present invention in use during patient transport.
Figures 7, 8:
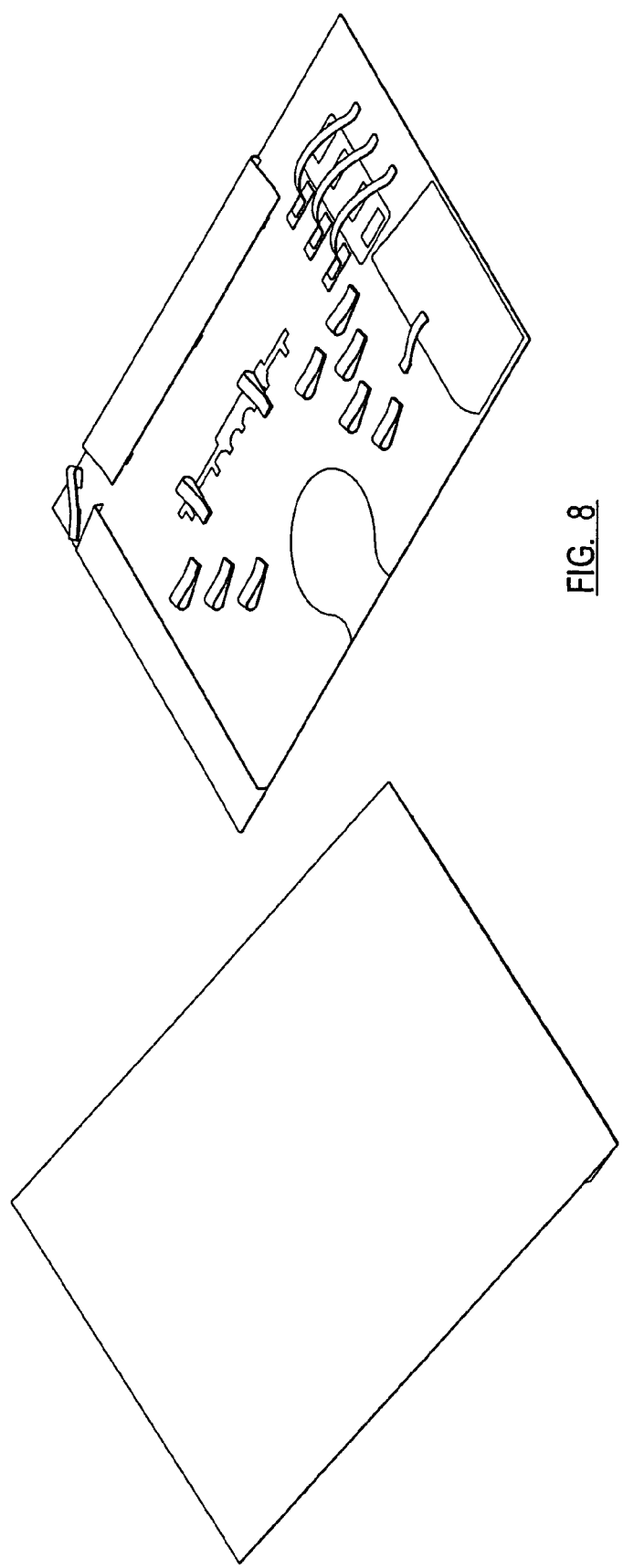
FIG. 7 is a bottom perspective view of an alternative embodiment of the present invention.
FIG. 8 is a top perspective view of the embodiment of FIG. 7.
Figure 9:
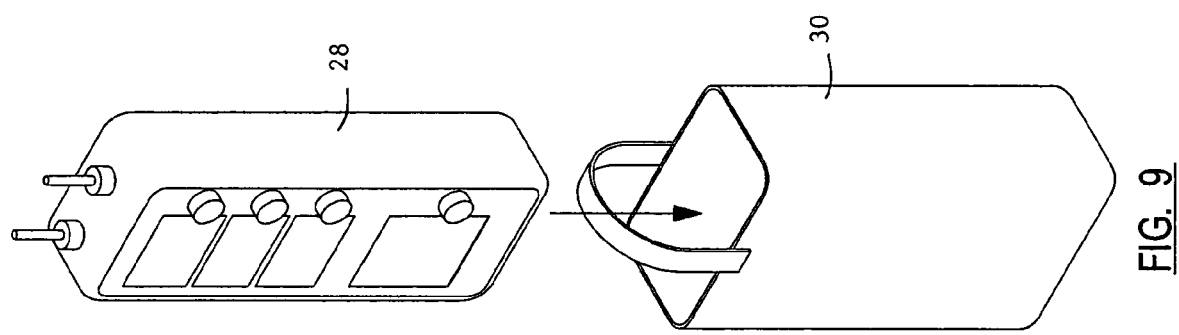
FIG. 9 is a perspective view of an accessory case for the present invention used to carry a pacemaker.

The upper surface of pad 21 may also be provided with one or more flaps or sleeves 24 that may be folded against pad 21 and held in place to surround a group or bundle of lines leading to/from the patient, as illustrated in FIG. 6. Flaps 24 may be closed using Velcro® strips, zippers, snaps, buttons or the like 26. The upper surface of pad 21 is also provided with one or more pockets for holding such things as a pacemaker, emergency medicine, emergency medical tools and/or other medical devices for use during patient transport. The pacemaker pocket 27 is closable, and designed to hold a pacemaker 28 and an optional carrying case 30 during patient transport. Additional holders 32 may also be provided to hold a 3-way transducer or other objects during transport.

Figure 2:
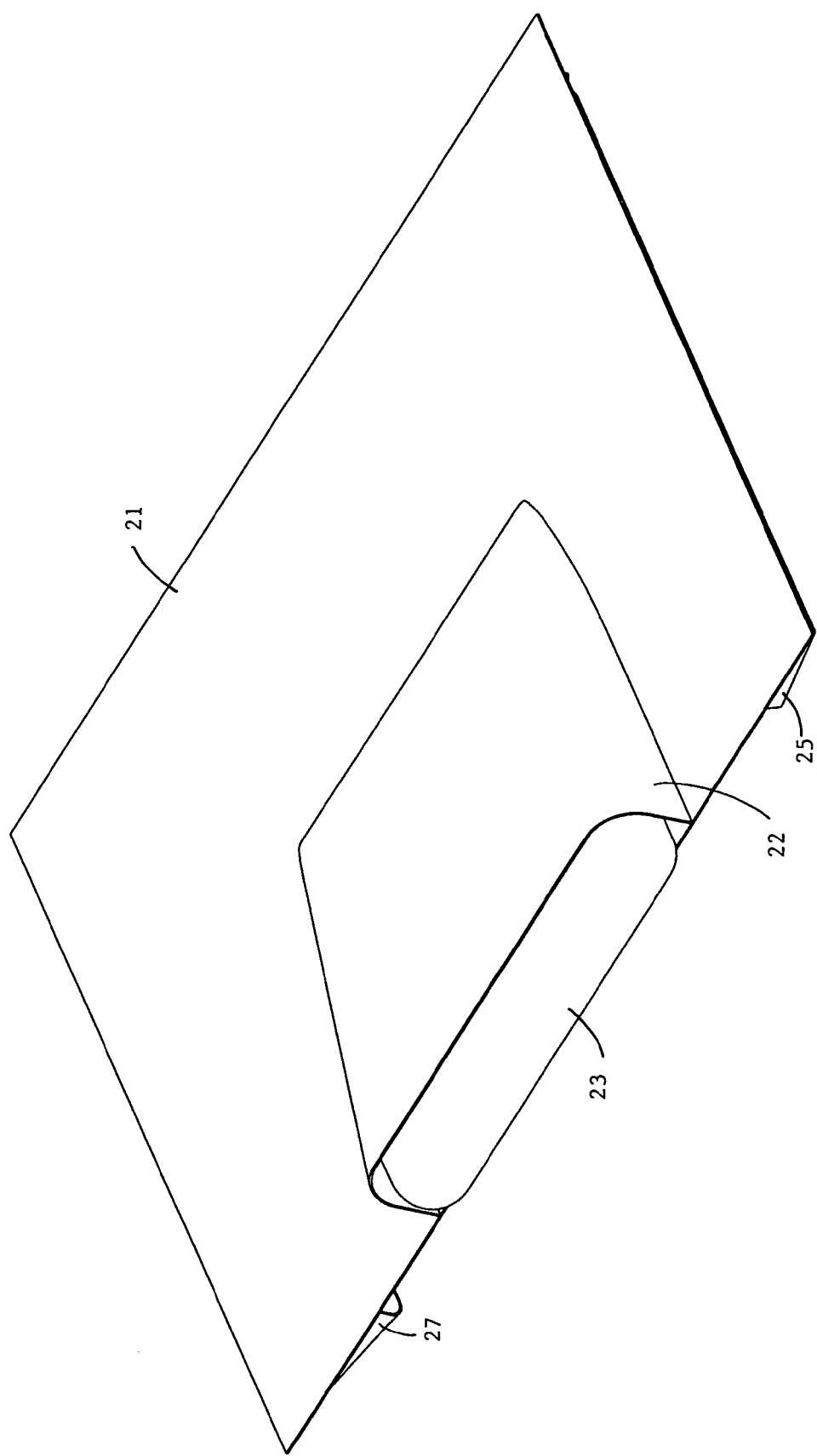
FIG. 2 is a bottom perspective view of the embodiment of FIG. 1.

A separate pocket 22 may be provided on the bottom surface of pad 21 for receiving a pillow 23 to support the patient's head, as shown in FIGS. 1-2.

Figure 3:
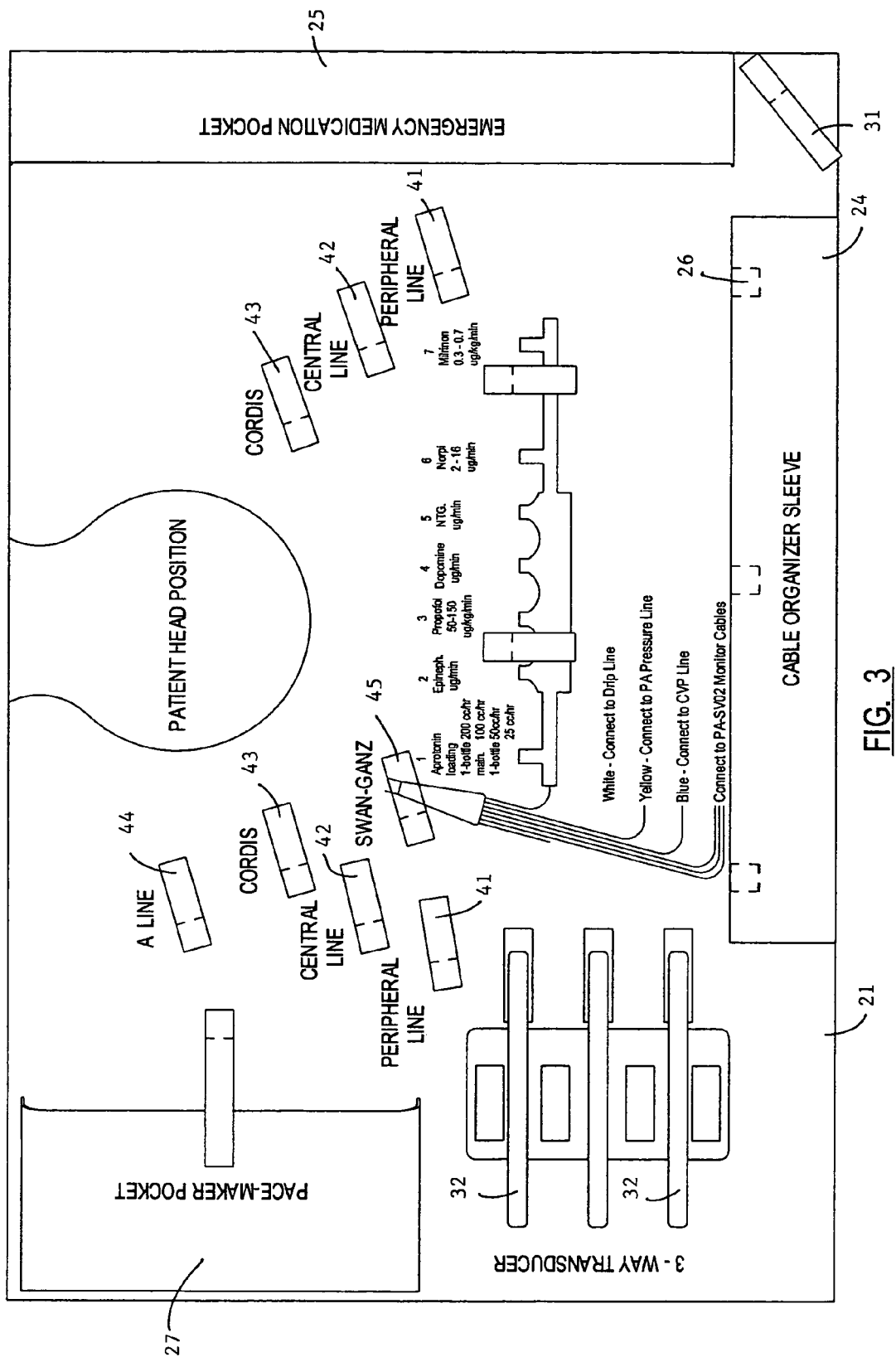
FIG. 3 is a top plan view along line 3-3 of FIG. 1 showing general labeling.

Referring to FIG. 3, it is seen that a more elaborate embodiment of pad 21 is provided with a plurality of specific holders for specific lines. These include holders that may be located on either or both sides of the patient's head for a peripheral line 41, central line 42, and cordis 43. Dual holders 41, 42 and 43 may be provided for the convenience of the anesthesiologist, since these lines may originate from either side of the patient's body, depending upon where the best attachment was obtained. However, certain lines such as the arterial line and Swan-Ganz catheter are conventionally located on the left side of the patient. Thus, holders 44 and 45 for the arterial line and Swan-Ganz catheter, respectively, are provided on the left side of pad 21, as shown in FIG. 3. Specific labeling for these holders 41-45 may be provided, as shown in FIG. 3.

Figure 4:
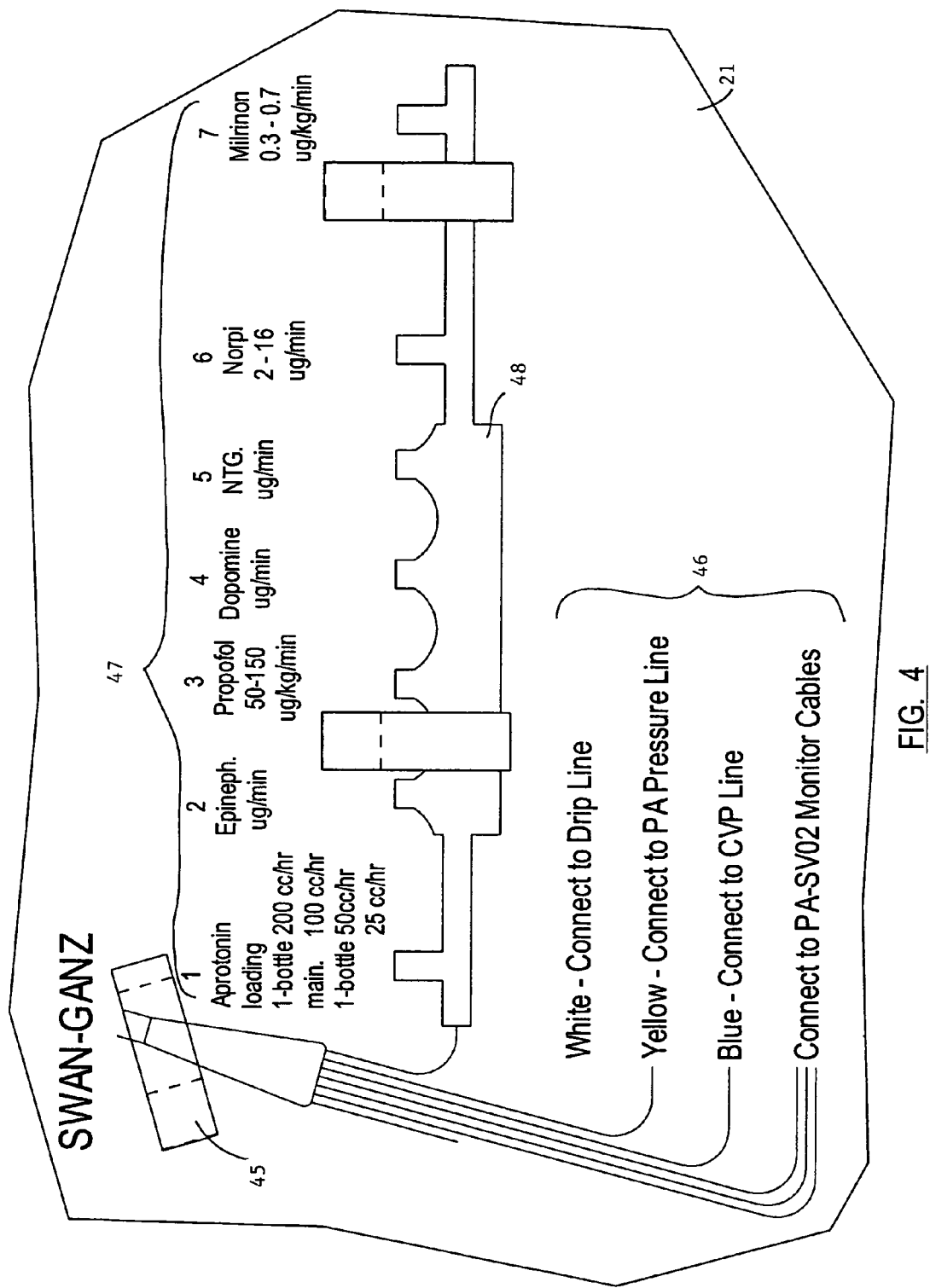
FIG. 4 is a detailed top view along line 4-4 of FIG. 1 showing an embodiment with specific labeling.

Referring to the labeled embodiment of FIGS. 3-4, it is seen that additional labeling 46 may also be provided to assist the anesthesiologist in making the proper connections from the Swan-Ganz catheter. In particular, the labeling may indicate that the white line is to be connected to one or more drip lines (or to a manifold), the yellow line is to be connected to the PA pressure line, the blue line is to be connected to the CVP line, and that 3 additional cables are to be connected to the PA and SVO2 monitors. Further labeling for the white line and commonly used medications, dosages and administration information 47 may also be provided as shown in FIG. 4. This labeling 47 may provide, for example, information for (1) aprotonin loading, 1-bottle 200 cc/hr; maintenance 100 cc/hr; 1-bottle 50 cc/hr; 25 cc/hr; (2) epineph μg/min; (3) propofol 50-150 μg/kg/min; (4) Dopomine μg/min; (5) NTG μg/min; (6) Norpi 2-16 μg/min; and Milrinan 0.3-0.7 μg/kg/min. A diagram 48 for a typical manifold may also be provided. This labeling 46 and 47 may be updated or revised as different devices, drugs and dosages are developed, or if different standards are adopted by practitioners.

At the beginning of surgery, as one end of each line (peripheral line, arterial line, central line, etc.) is attached to the patient, the anesthesiologist attaches the opposite end of the line to its appropriate location. The anesthesiologist then engages the particular line with a holder on the pad (e.g., holders 41, 44 and 42, respectively, in the above example). In certain embodiments of the present invention, the pad will already have labels and/or color coding adjacent to the holders for each of these major lines. In other embodiments, the anesthesiologist may apply the labels to the pad or holders. In other embodiments, additional labels are provided for attachment to the lines up near their proximal ends. These will generally be duplicate labels, and may also be color coded (to match or complement the color coding of the holders on the pad), and may include pre-printed labels, and may also include adhesive for easy attachment. If a Swan-Ganz catheter is used, it is attached to its own holder 45, and the lines extending from this catheter are connected to appropriate medical devices or bags. In certain embodiments of the present invention, the pad will already have labels and/or color coding for these connections 46 as shown in the exemplary embodiment of FIG. 4. The pad may also include specific medication dosage and administration information for drips or other inputs to the white line 47, also detailed in the exemplary embodiment of FIG. 4.

Figure 5:
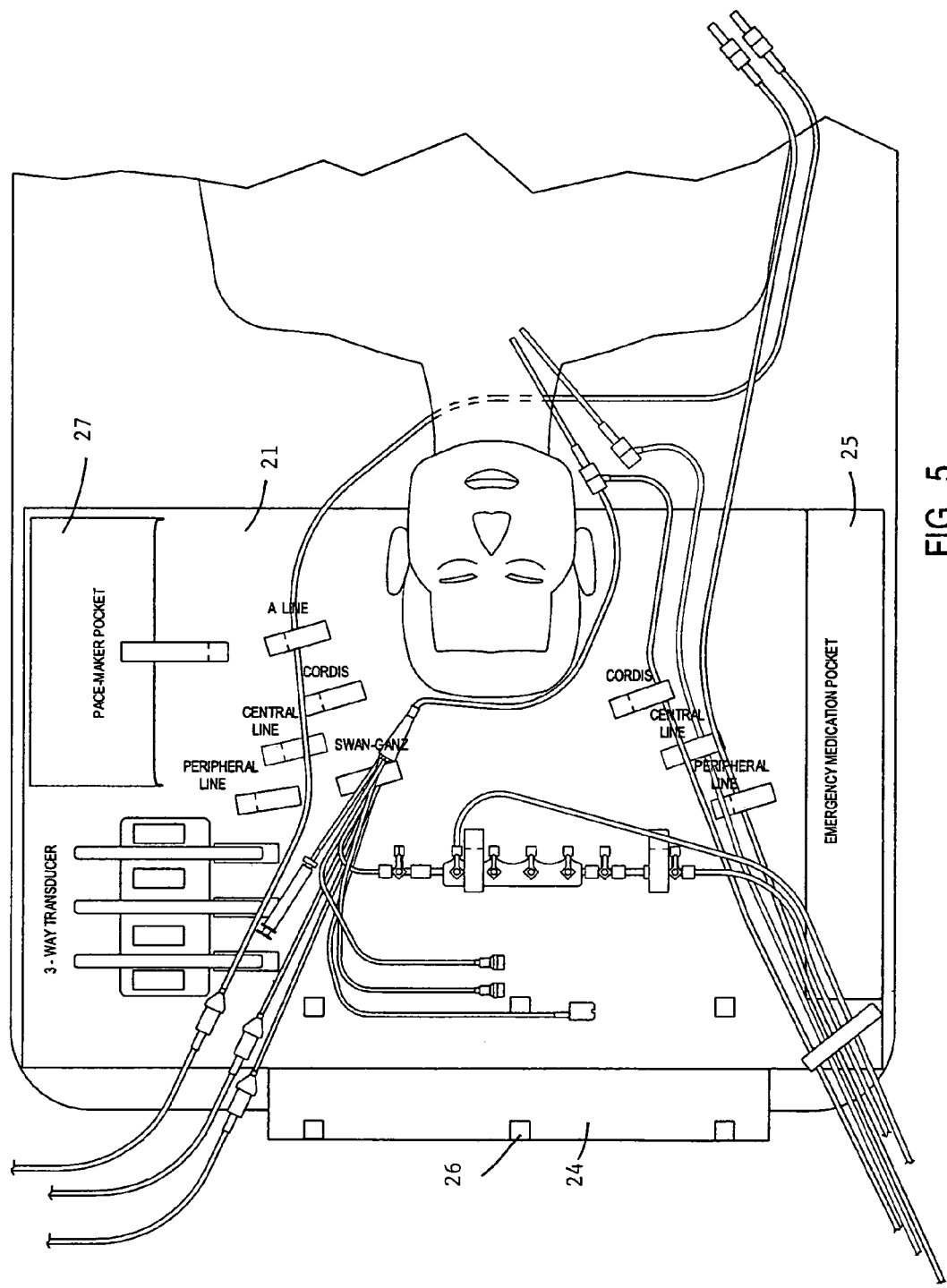
FIG. 5 is a top perspective view of an embodiment of the present invention in use during a surgery.

FIG. 5 shows a labeled embodiment of pad 21 of the present invention in use during surgery. Holders 41-45 have been attached to the lines leading from the patient, and the Swan-Ganz catheter ports have been connected to the various devices. Should the patient have a need for medication, the anesthesiologist can instantly identify the proper line and administer the proper dose of the required medication. Should the anesthesiologist be relieved by another physician, or should this be a training situation for a resident, fellow or new physician, the pad of the present invention allows that person to immediately locate and utilize all of these critical lines. This will help the anesthesiologist or the replacement person to avoid time consuming delays and potential errors in administration of drugs and anesthesia.

After all of the lines are connected, in order to maintain organization and avoid entanglement or confusion during and after surgery, the anesthesiologist may bundle together groups of lines going in the same general direction, and attach them to corner holders such as 31, or fold these bundles of lines into flaps 24 located at the edges of the pad 21. These flaps 24 are provided with Velcro®, snaps, buckles, buttons or other attachment devices to hold them against pad 21 with the bundle of lines inside, as shown in FIG. 6.

Figure 10:
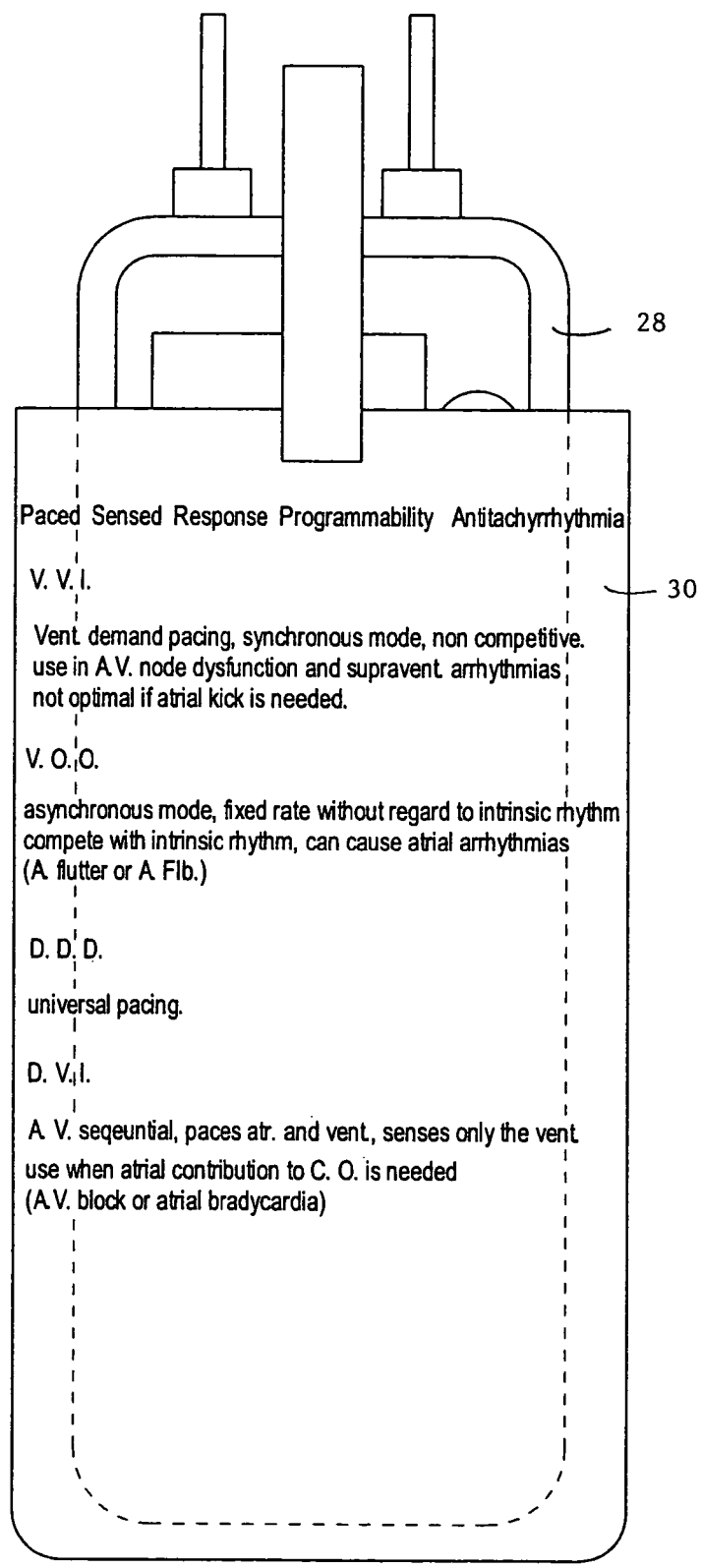
FIG. 10 is a detailed front elevational view of the case of FIG. 9 illustrating instructions for the pacemaker.

In one embodiment, a pouch 30 is provided for holding the pacemaker 28. It is to be appreciated that the wires leading from the patient to the pacemaker generally travel overhead and are not attached to the pad of the present invention. The pouch 30 with pacemaker 28 may be hung from a pole, and then taken down and placed in a pocket 27 during patient transport. In an alternative embodiment, an example of which is shown in FIG. 10, specific instructions regarding the use and programming modes for the pacemaker are provided on the outside of the pouch to assist the anesthesiologist in setting up this device during and after surgery. These may include, but are not limited to the following:

| Paced Sensed Response Programmability Antitachyrrhythmia |
| --- |
| V.V.I. |
| Vent demand pacing, synchronous mode, non competitive. use in A.V. mode dysfunction and supravent and arrhythmias not optional if atrial kick is needed. |
| V.O.O. |
| asynchronous mode, fixed rate without regard to intrinsic rhythm compete with intrinsic rhythm, can cause atrial arrhythmias (A. flutter or A. Fib.) |
| D.D.D. |
| universal pacing |
| D.V.I. |
| A.V. sequential, paces atr. and vent, senses only the vent use when atrial contribution to C.O. is needed (A.V. block or atrial bradycardia) |

Upon completion of surgery, the pad of the present invention is designed to travel with the patient to recovery and/or intensive care, and to remain with the patient for hours, days or even weeks. It is preferred that a durable rubberized (or plastic) version of the pad of the present invention be used for lengthy patient recoveries, with paper or film versions used for shorter recoveries. The pad may also be made of suitable webbing, the thickness thereof depending on the length of anticipated recovery.

In order to prepare for transport, among other things the pacemaker 28 is removed from the pole it is hanging on, and placed into pocket 27 to prevent dislodgement of its wires during transport. The transducer 36 is detached from its overhead monitor(s) and attached to pad 21 using straps 31. Emergency medication and tools (such as a laryngoscope and endotracheal tube) are inserted into pocket 25. The 3 monitor lines from the Swan-Ganz catheter are disconnected from their overhead monitors, but one line may be connected to a portable blood pressure monitor that travels with the patient. Then the patient is moved to recovery or intensive care along with the connected drip lines, etc. Should blood pressure drop, or any other situation arise during transport, pockets 25 allow the necessary tools to be available for the medical staff. The pad and holders of the present invention also secure the lines, preventing inadvertent dislodgement or disengagement of the tubes and lines from the patient during the movement associated with travel. Upon arrival, the disconnected lines and cables may be easily and quickly identified and attached to their respective monitors and sources. The pad may remain with the patient for hours, days or weeks, as necessary, to maintain the organization of these lines and tubes.

It is to be appreciated that a smaller dimensioned version of the present invention may be used in pediatric and neonatal applications.

Further, although the invention has been described in terms of exemplary embodiments, it is not limited thereto. Rather, the appended claims should be construed broadly, to include other variants and embodiments of the invention which may be made by those skilled in the art without departing from the scope and range of equivalents of the invention.

What is claimed is:

1. A coordination device for use by an anesthesiologist comprising:

a generally flat, flexible pad for placement beneath the head of a patient during the providing of anesthesia, the pad having an upper and a lower surface, a diagram on the upper surface indicating a head placement area sized and positioned for placement of the patient's head thereon, and a top periphery;

a plurality of holders on said upper surface;

said plurality of holders including a plurality of line holders surrounding the head placement area on the upper surface for receiving a plurality of lines attached to the patient's body and for maintaining the positions of the plurality of lines relative to the patient's head and body for visually presenting the physical arrangement of the plurality of lines relative to the patient and the left or right side location of connection of each of the plurality of lines to the patient, and said plurality of line holders including:

a first line holder labeled as ARTERIAL LINE and color coded red and positioned on the left side of the head placement area;

a second line holder labeled as CORDIS and positioned on the left side of the head placement area;

a third line holder labeled as CORDIS and positioned on the right side of the head placement area;

a fourth line holder labeled as CENTRAL LINE color coded blue and positioned on the left side of the head placement area;

a fifth line holder labeled as CENTRAL LINE color coded blue and positioned on the right side of the head placement area;

a sixth line holder labeled as PERIPHERAL LINE and positioned on the left side of the head placement area;

a seventh line holder labeled as PERIPHERAL LINE and positioned on the right side of the head placement area; and an eighth line holder labeled as SWAN-GANZ and color coded yellow and positioned towards the left side of the head placement area;

said plurality of holders further including a plurality of drug line holders for receiving and maintaining the positions of lines used to deliver drugs to the patient and each of said plurality of drug line holders being labeled to identify a specific intraoperative drug and drug dosage unit of measurement corresponding with the identified drug;

said plurality of holders further including at least one holder for holding a medical device on the upper surface of the flat flexible pad; and a sleeve along the top periphery of said pad for supporting a coiled arrangement of the plurality of lines above a floor surface.

2. The coordination device of claim 1 wherein said plurality of line holders are fixedly attached to said pad.

3. The coordination device of claim 2 wherein said plurality of line holders are each releasably secured by hook and loop fasteners to hold the identified line in place on said pad.

4. The coordination device of claim 1 wherein said pad is made of a flexible material selected from the group consisting of a rubberized sheet, durable plastic, webbing and heavy paper.

5. The coordination device of claim 1 further comprising:

at least one pocket on the upper surface of said pad for holding a medical device.

6. A coordination device for use by an anesthesiologist comprising:

a generally flat, flexible pad for placement beneath the head of a patient during the providing of anesthesia, the pad having an upper and a lower surface, a diagram on the upper surface indicating a head placement area sized and positioned for placement of the patient's head thereon, and a top periphery;

a plurality of holders on said upper surface;

said plurality of holders including a plurality of line holders surrounding the head placement area on the upper surface for receiving a plurality of lines attached to the patient's body and for maintaining the positions of the plurality of lines relative to the patient's head and body for visually presenting the physical arrangement of the plurality of lines relative to the patient and the left or right side location of connection of each of the plurality of lines to the patient, and said plurality of line holders including:

a first line holder labeled as ARTERIAL LINE and positioned on the left side of the head placement area;

a second line holder labeled as CORDIS and positioned on the left side of the head placement area;

a third line holder labeled as CORDIS and positioned on the right side of the head placement area;

a fourth line holder labeled as CENTRAL LINE and positioned on the left side of the head placement area;

a fifth line holder labeled as CENTRAL LINE and positioned on the right side of the head placement area;

a sixth line holder labeled as PERIPHERAL LINE and positioned on the left side of the head placement area;

a seventh line holder labeled as PERIPHERAL LINE and positioned on the right side of the head placement area; and an eighth line holder labeled as SWAN-GANZ and positioned towards the left side of the head placement area;

said plurality of holders further including a plurality of drug line holders for receiving and maintaining the positions of lines used to deliver drugs to the patient and each of said plurality of drug line holders being labeled to identify a specific intraoperative drug and drug dosage unit of measurement corresponding with the identified drug;

said plurality of holders further including at least one holder for holding a medical device on the upper surface of the flat flexible pad; and a sleeve along the top periphery of said pad for supporting a coiled arrangement of the plurality of lines above a floor surface.

7. The coordination device of claim 6 wherein said plurality of line holders are color coded.

8. The coordination device of claim 7 wherein said plurality of line holders are fixedly attached to said pad.

9. The coordination device of claim 8 wherein said plurality of line holders are each releasably secured by hook and loop fasteners to hold the identified line in place on said pad.

10. The coordination device of claim 6 wherein said pad is made of a flexible material selected from the group consisting of a rubberized sheet, durable plastic, webbing and heavy paper.

11. The coordination device of claim 7 further comprising:
at least one pocket on the upper surface of said pad for holding a medical device.

* * * * *